United States Patent
Wakayama

[11] Patent Number: 6,016,438
[45] Date of Patent: Jan. 18, 2000

[54] MPR IMAGE CREATING APPARATUS AND COAXIAL TOMOGRAM CREATING METHOD THEREIN

[75] Inventor: Kento Wakayama, Tochigi, Japan

[73] Assignee: Kabushiki Kaisha Toshiba, Kawasaki, Japan

[21] Appl. No.: 08/953,990

[22] Filed: Oct. 20, 1997

[30] Foreign Application Priority Data

Oct. 21, 1996 [JP] Japan .................................. 8-278166

[51] Int. Cl.[7] .................................................. A61B 5/055
[52] U.S. Cl. .......................... 600/410; 324/307; 324/309
[58] Field of Search ............................ 600/410; 324/307, 324/309

[56] References Cited

U.S. PATENT DOCUMENTS

| Re. 35,798 | 5/1998 | Kimura | 128/920 |
|---|---|---|---|
| 4,835,688 | 5/1989 | Kimura | 128/920 |
| 5,315,665 | 5/1994 | Ohhashi | 382/128 |
| 5,848,126 | 12/1998 | Fujita et al. | 378/195 |
| 5,907,592 | 5/1999 | Levinson | 378/144 |

FOREIGN PATENT DOCUMENTS

| 40322454 | 10/1991 | Japan . |
|---|---|---|
| 07255713 | 10/1995 | Japan . |

*Primary Examiner*—Brian L. Casler
*Attorney, Agent, or Firm*—Oblon, Spivak, McClelland, Maier & Neustadt, P.C.

[57] ABSTRACT

MPR images are displayed on a display, and when a coaxial tomogram to be obtained (for example, axial image) is specified and a range and pitch of coaxial tomograms to be obtained are set on a sagital image, for example, the coaxial tomograms (for example, axial image) whose number is determined by the range and pitch can be obtained. Moreover, when a plurality of obtained coaxial tomograms are successively displayed on the display and a save button is operated on a desired coaxial tomogram, only the desired coaxial tomogram can be saved.

11 Claims, 10 Drawing Sheets

MPR IMAGE CREATING APPARATUS AND COAXIAL TOMOGRAM CREATING METHOD THEREIN

BACKGROUND OF THE INVENTION

1. Field of the Invention

The present invention relates to an MPR image creating apparatus and a coaxial tomogram creating method therein, and more specifically relates to an MPR image creating apparatus in which when a desired range of a sagital image, for example, is specified, an axial image corresponding to the sagital image can be obtained easily, and to a coaxial tomogram creating method therein.

2. Prior Art

MPR (multi-planar reconstruction, cross section inversion) is a function for creating a coronal image, sagital image, axial image and oblique image, etc., based on an original image data obtained by a CT apparatus, for example.

Figure 1:
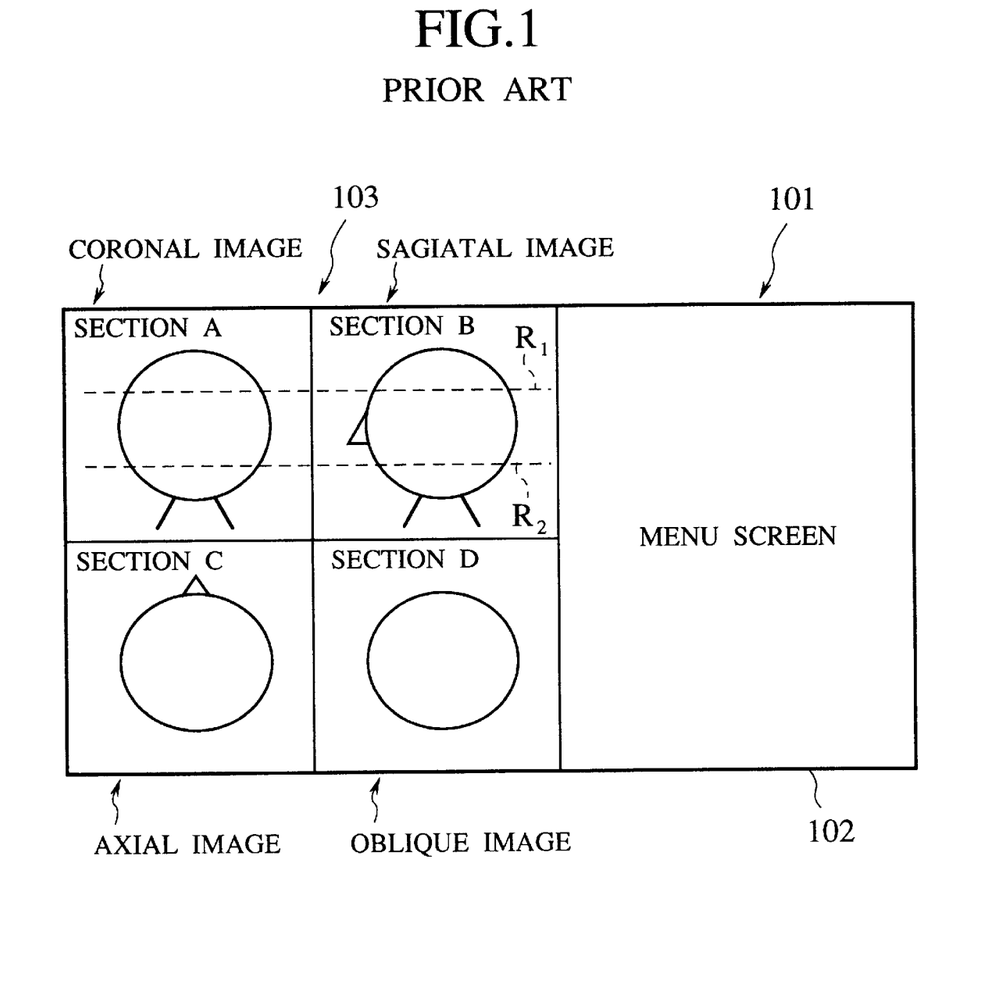
FIG. 1 is a drawing explaining a method of obtaining a desired cross sectional image in a conventional MPR image display screen.

FIG. 1 is a drawing which explains a method of obtaining a desired cross sectional image in a conventional MPR image creating apparatus.

In FIG. 1, 101 is a display which is capable of specifying and inputting by a mouse or the like, and the display 101 is provided with a menu screen display section 102 for displaying a menu screen for inputting various screen operating information (mentioned later), and an MPR image display section 103 for displaying an MPR image such as a sagital image.

The MPR image display section 103 is divided into four, i.e., sections A through D. A coronal image of a human head, for example, is displayed on the section A on the upper left part, a sagital image on the section B on the upper right part, an axial image on the section C on the lower left part, and an oblique image on the section D on the lower right part.

Figure 2:
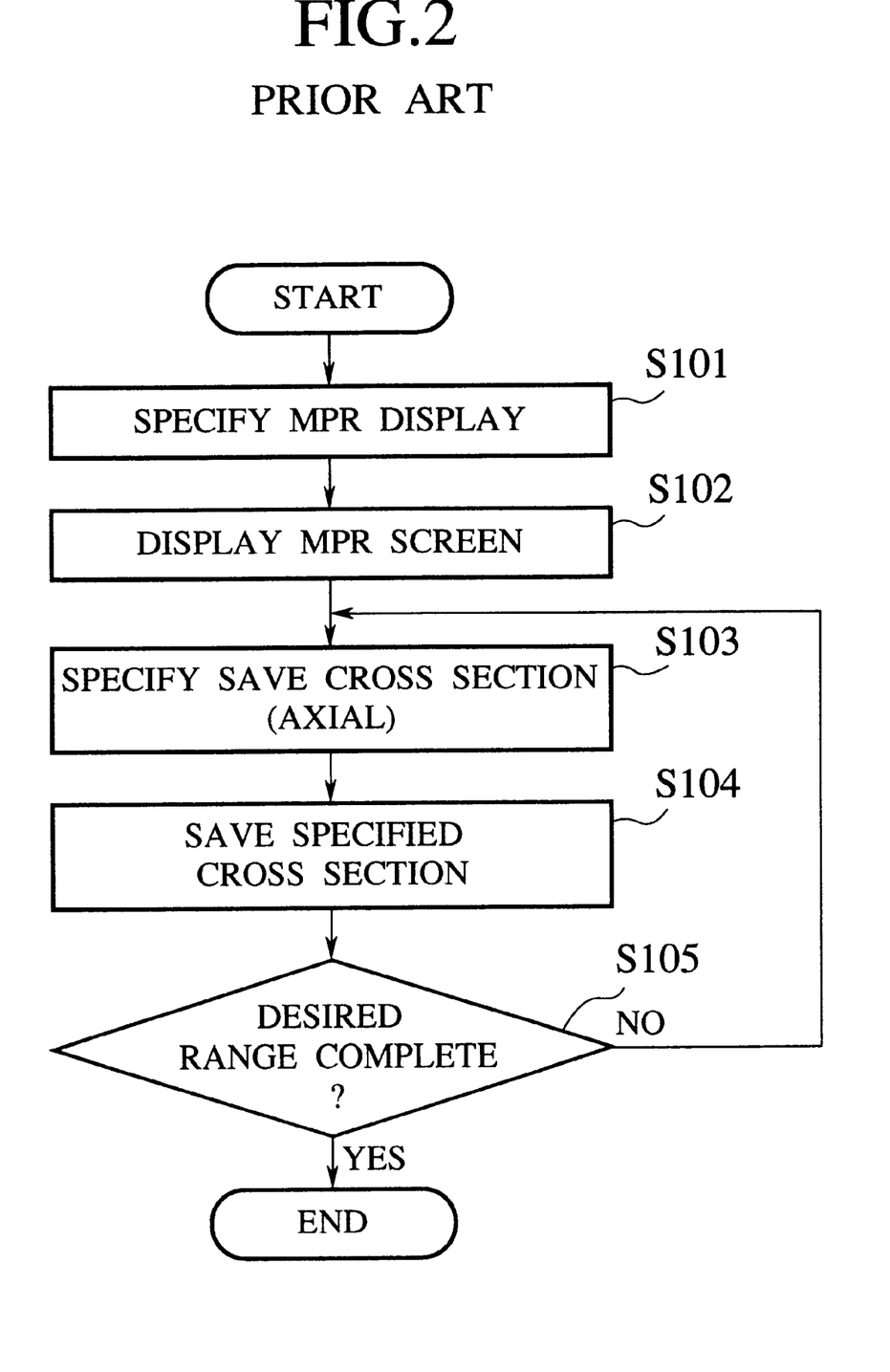
FIG. 2 is a flow chart showing a processing sequence of obtaining the desired cross sectional image in the conventional MPR cross sectional image.

In the case where a doctor wants to save the axial image in a desired range of the displayed sagital image, an operation shown in FIG. 2, for example, was performed on the menu screen 102.

Namely, when MPR display is specified (S101), the coronal image, sagital image, axial image and oblique image are simultaneously displayed on the MPR image display section 103 (see FIG. 1) (S102). When a cross section on the axial image (section C) which is desired to be saved is specified on the sagital image on the section B by a cursor (represented by an arrow $R_1$) (S103), only one specified axial image is saved (S104).

In the case where ten axial images are desired to be saved until the range on the section B represented by an arrow $R_2$, it was necessary to repeat the steps S101 through S104 ten times (S105).

In addition, in the case where the axial image is created and displayed other than the above case of saving the axial image, it was necessary to specify creation and display of the axial images one by one.

However, it was troublesome that in order to obtain the desired axial images in the above-mentioned manner, an operator such as a doctor repeats operational input such as saving, creating and displaying the axial images one by one.

SUMMARY OF THE INVENTION

It is an object of the present invention to provide an MPR image creating apparatus in which when a desired cross sectional image is obtained, a desired number of the cross sectional images in a desired range can be obtained by a few operations, and to provide a coaxial tomogram creating method in the apparatus.

In order to achieve the above object, there is provided an MPR image creating apparatus comprising: MPR image creating means for creating at least not less than two coaxial tomograms in different slice directions as MPR images, MPR image display means for displaying the MPR images created by the MPR image creating means, creating condition set control means for setting a creating condition of one MPR image displayed on the MPR image display means, and coaxial tomogram creating means for creating coaxial tomograms corresponding to the MPR image whose creating condition has been set based on the creating condition set by the creating condition set control means.

According to the present invention, when the creating condition of a displayed sagital image, for example, is set, a plurality of axial images are created according to the creating condition. Therefore, when an arbitrary creating condition is set, arbitrary coaxial tomograms can be obtained.

In preferable embodiment of the present invention, the creating condition set control means sets a range and pitch of the coaxial tomograms to be obtained as the creating condition.

According to this embodiment, the coaxial tomograms whose number is determined by the range and pitch can be obtained. Particularly when an angle is specified as the range, an oblique image is obtained.

In preferable embodiment of the present invention, the creating condition set control means sets a range and number of the coaxial tomograms to be obtained as the creating condition.

According to this embodiment, a plurality of coaxial tomograms having a pitch determined by the range and number are obtained.

In preferable embodiment of the present invention, a buffer for temporarily storing the coaxial tomograms created by the coaxial tomogram creating means is further provided.

In preferable embodiment of the present invention, tomograms created by the coaxial tomogram creating means is further provided.

In preferable embodiment of the present invention, the coaxial tomogram display means successively displays a plurality of coaxial tomograms stored in the buffer.

According to this embodiment, an operator can confirm a plurality of obtained coaxial tomograms.

In preferable embodiment of the present invention, the coaxial tomogram display means comprisies display speed set means for setting a display speed, when a plurality of the coaxial tomograms are successively displayed.

In preferable embodiment of the present invention, coaxial tomogram specifying means for specifying an arbitrary image of a plurality of the coaxial tomograms created by the coaxial tomogram display means is further provided.

In preferable embodiment of the present invention, storage means for storing the coaxial tomogram specified by the coaxial tomogram specifying means is further provided.

According to this embodiment, only specified coaxial tomogram of a plurality of the obtained coaxial tomograms is specified and stored in the storage means.

In order to achieve the above object, there is provided a coaxial tomogram creating method in an MPR image creating apparatus comprising the steps of creating at least not less than two coaxial tomograms in different slice directions as MPR images, displaying the created MPR images, setting a creating condition of one displayed MPR image, and creating coaxial tomograms corresponding to the MPR image whose creating condition has been set based on the creating condition.

For a fuller understanding of the nature and advantages of the invention, reference should be made to the ensuing detailed description taken in conjunction with the accompanying drawings.

DETAILED DESCRIPTION OF THE PREFERRED EMBODIMENTS

The following describes embodiments of the MPR image creating apparatus of the present invention in detail on reference to the drawings.

Figure 3:
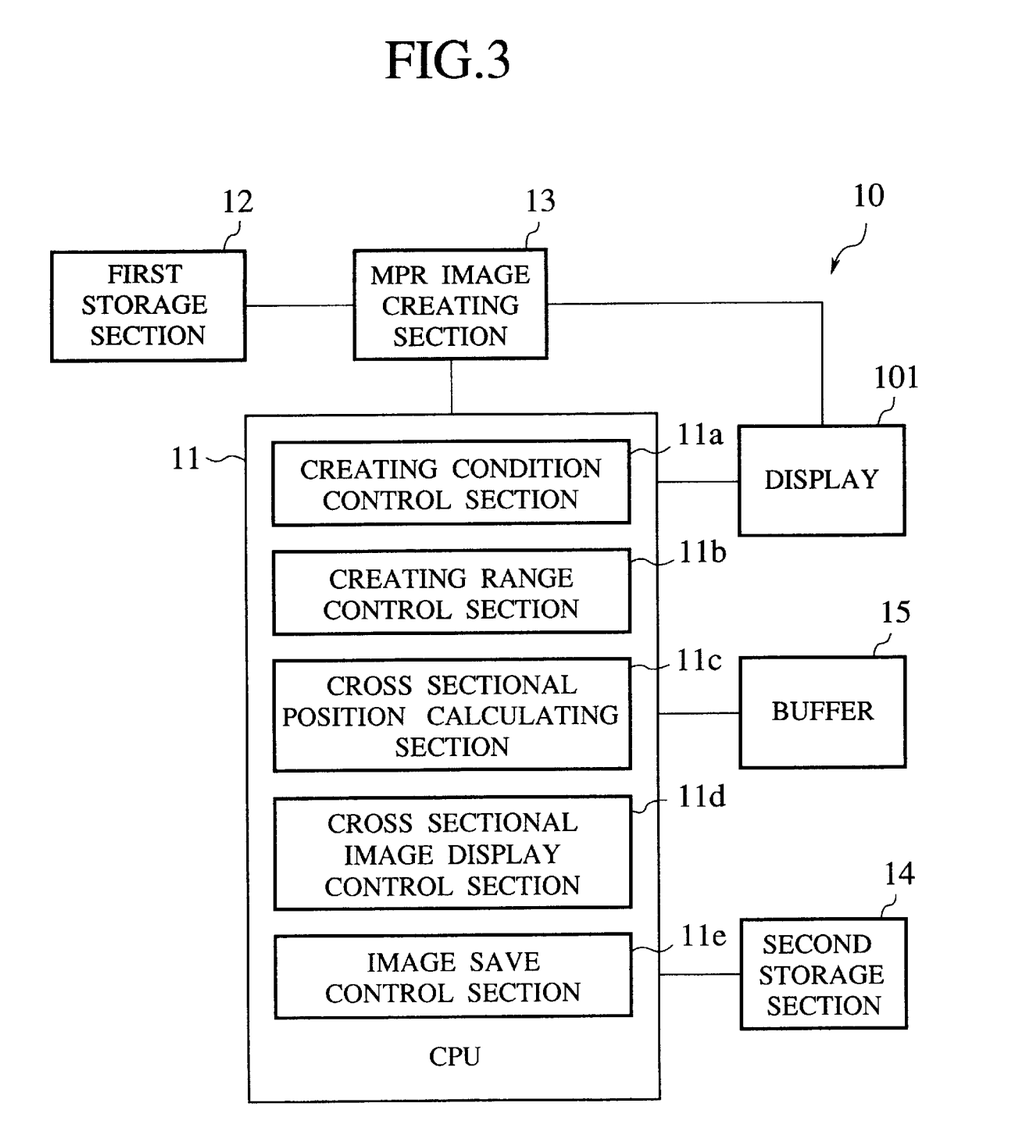
FIG. 3 is a block diagram of an MPR image creating apparatus according to one embodiment of the present invention.

FIG. 3 is a block diagram of the MPR image creating apparatus according to one embodiment of the present invention.

First, the description will be given as to the arrangement of the MPR image creating apparatus.

As shown in FIG. 3, an MPR image creating apparatus 10 is provided with a central processing unit (CPU) 11 having various control sections, mentioned later, a first storage section 12, an MPR image creating section 13, a display 101, a buffer 15, a second storage section 14, etc. The first storage section 12 stores original image data such as a CT image and MRI image created by a CT unit, MRI unit, etc. (not shown) thereinto. The MPR image creating section 13 creates an MPR image such as a sagital image from original image data stored in the first storage section 12. The display 101 displays an MPR image and a menu screen, mentioned later. The buffer 15 temporarily saves a plurality of the obtained MPR images. The second storage section 14 saves a specified MPR image.

The CPU 11 has a creating condition control section 11a, a creating range control section 11b, a cross sectional position calculating section 11c, cross sectional image display control section lid and image save control section 11e. The creating condition control section 11a specifies and controls a creating condition (for example, a sagital image is specified so that an axial image is created) of the specified cross sectional image. The creating range control section 11b controls a creating range of the specified cross sectional image. The cross sectional position calculating section 11c calculates a position of the specified cross sectional image. The cross sectional image display control section lid controls display of the cross sectional image in the position calculated by the cross sectional position calculating section 11c. The image save control section lie controls saving of the cross sectional image.

(1) First Embodiment

The following describes an operation of the present embodiment reference to FIGS. 4 through 9.

Figure 4:
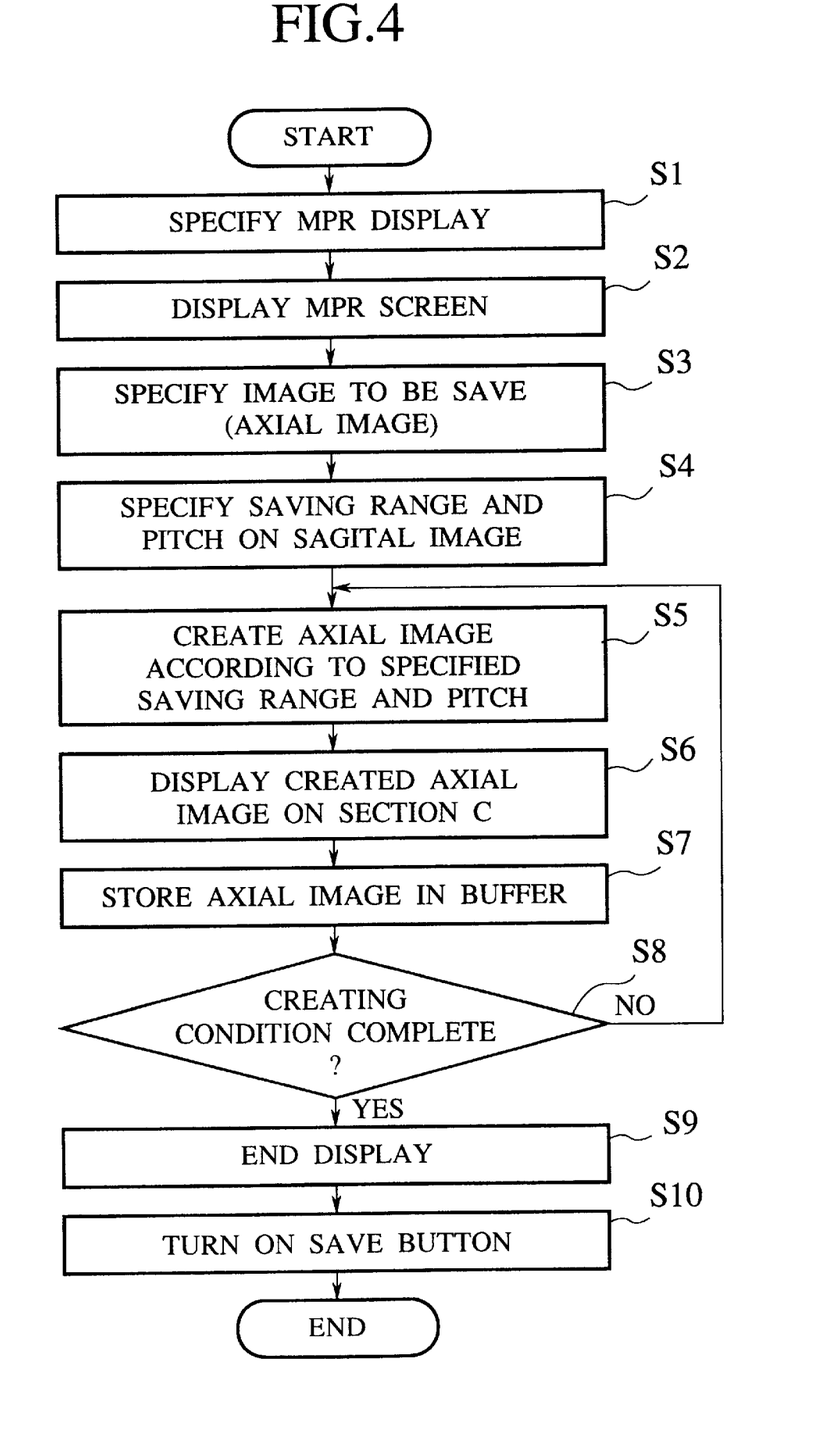
FIG. 4 is a flow chart showing a processing sequence in the case where a sagital image is specified so that an axial image is obtained in a first embodiment.
Figure 5:
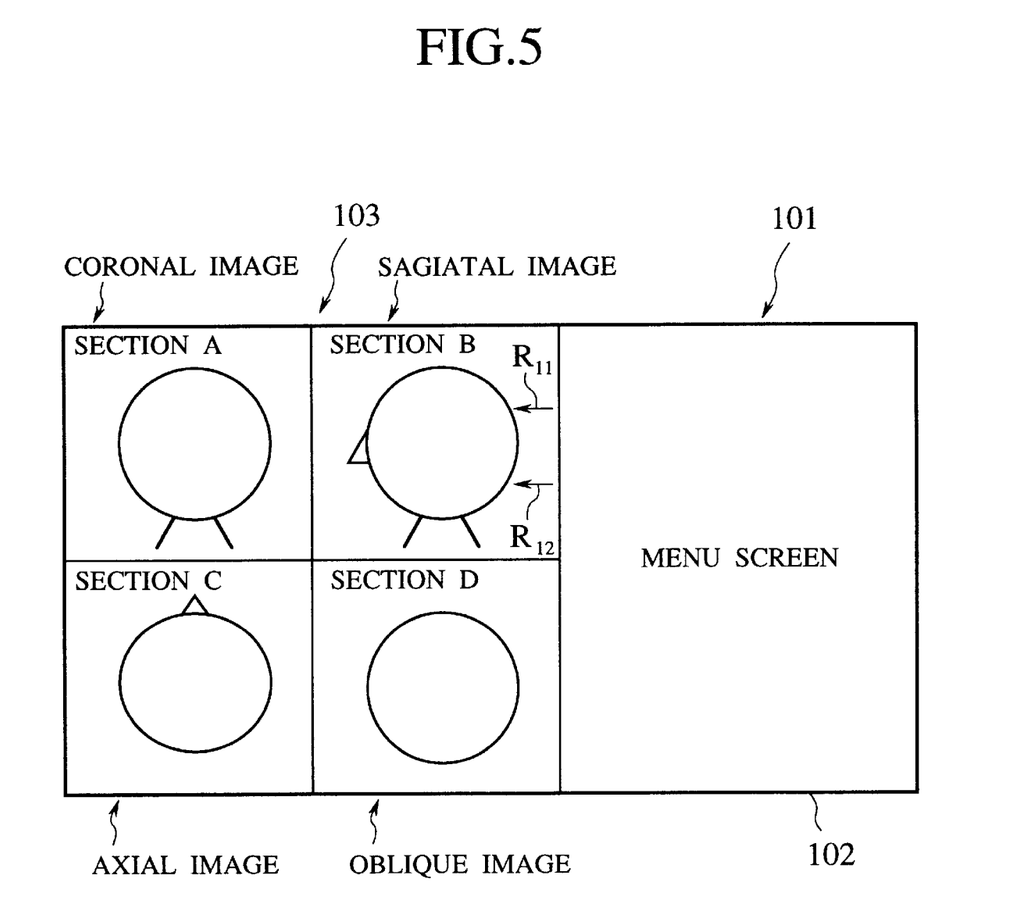
FIG. 5 is a drawing showing a display in the case the sagital image is specified so that the axial image is obtained in the first embodiment.
Figure 6:
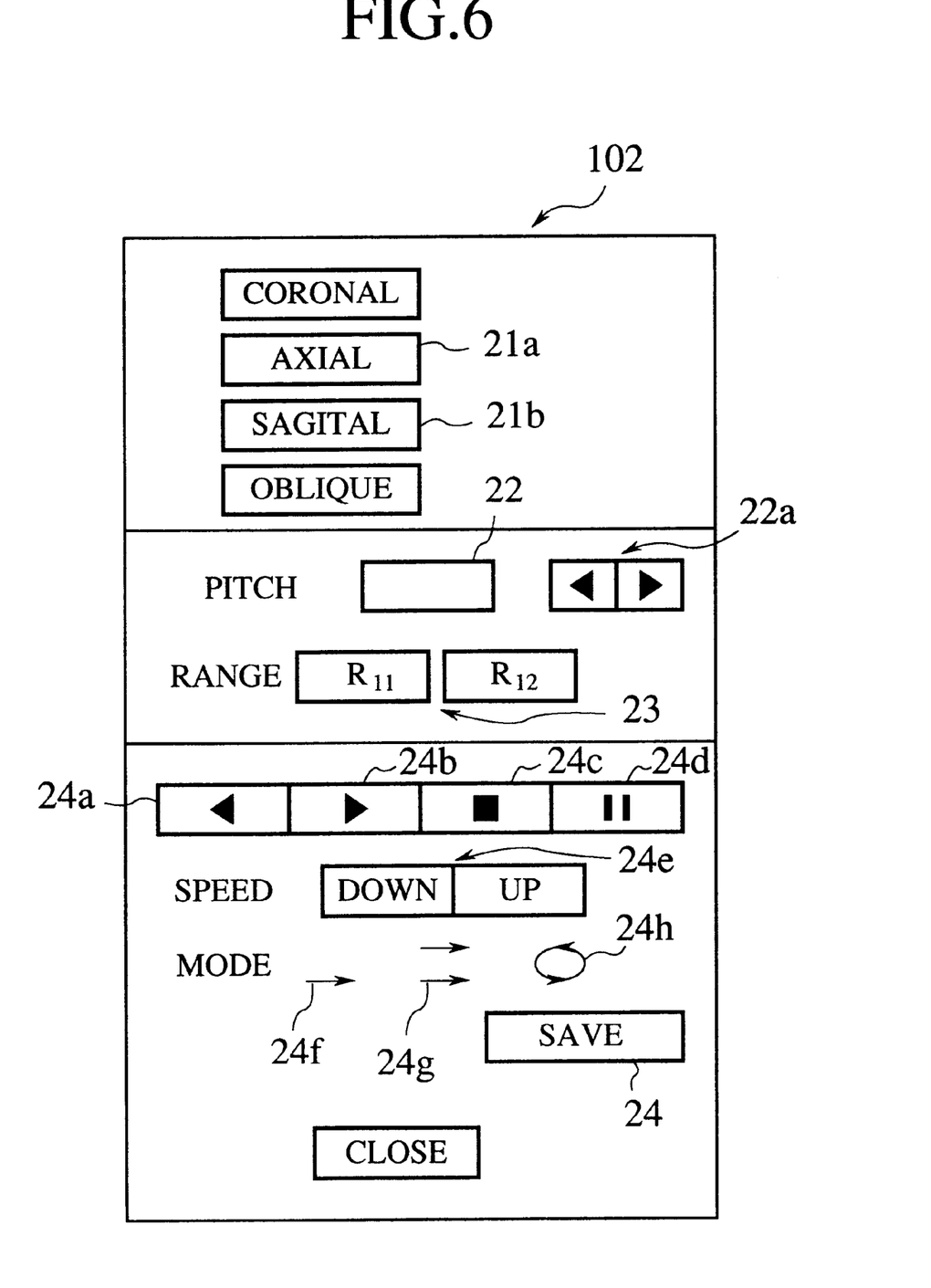
FIG. 6 is a drawing showing a menu screen display on the display.

FIG. 4 is a flow chart showing a processing sequence in the case where a sagital image is specified so that an axial image is obtained in a first embodiment. FIG. 5 is a drawing showing a display in the case where the sagital image is specified so that the axial image is obtained in the first embodiment. FIG. 6 is a drawing showing a menu screen displayed on the display.

In FIG. 5, 101 is a display on which specifying and input are possible by a mouse or the like, and a menu screen display section 102 and an MPR image display section 103 are formed on the display 101. On the menu screen display section 102, the menu screen for inputting various screen operating information (mentioned later) is displayed, and on the MPR image display section 103, an MPR image such as a sagital image is displayed.

The MPR image display section 103 is divided into four, i.e., sections A through D. A coronal image of a human head, for example, is displayed on the section A on the upper left part, a sagital image on the section B on the upper right part, an axial image on the section C on the lower left part, and an oblique image on the section D on the lower right part.

First, when an operator such as a doctor specifies MPR display using an MPR display specifying button (not shown) provided on the menu screen (FIG. 6) (S1), the MPR image shown in FIG. 5 is displayed (S2). Then, in order to specify the axial image (section C) as an image which is desired to be saved, an axial button 21a (FIG. 6) is indicated by a cursor (not shown) (S3).

Thereafter, it is specified and inputted on a range specifying section (FIG. 6) that a desired range of the image to be saved (axial image) is between positions $R_{11}$ and $R_{12}$ of the coronal image on the section A or the sagital image on the section B, and a pitch of the cross sections of the axial image is specified and inputted on a pitch specifying section 22 (S4). As a result, the cross sectional position calculating section 11c (FIG. 3) creates axial images according to the specified and desired range and pitch (creating condition) (S5). Here, the pitch and range of the cross sections to be saved can be set arbitrarily.

The created first axial image is displayed on the section C (S6), and the axial image is stored in the buffer 15 (S7). These steps are repeated until the desired range and pitch are completed (S8).

After the sequence is completed in the case of the specified creating conditions (S8; YES), the completion of creating the axial images according to the specified creating condition is displayed (S9), and when a save button 24 is turned ON, the axial images according to the specified creating condition (for example, 35 images) are simultaneously stored in the second storage section 14 (S10). Moreover, besides the simultaneous storage, as mentioned later, only specified axial images can be selectively stored in the second storage section 14.

In FIG. 6, 22a is a button which specifies increase and reduction of the pitch, 24a is a back feeding button, 24b is a screen forward feeding button, 24c is a screen-feeding stop button, and 24d is a screen-feeding temporary stop button. 24e is a screen-feeding speed up/down button (speed button), 24f is a single-feeding mode button, 24g is a repetitional feeding mode button, and 24h is a button which specifies a mode for alternate forward feeding and back feeding (loop reproducing mode button).

These respective buttons are operated by a cursor through a mouse or the like. For example, in the case where an operator wants to loop-reproduce a plurality of images stored in the buffer and to confirm whether or not the created axial images are suitable, and in the case where the operator wants to store only a specified image into the second storage section 14, the following operation should be performed.

Namely, for example, when the loop reproducing mode button 24h is selected and the forward feeding button 24b is selected, the axial images are loop-reproduced at the speed set by the speed button 24e. When the operator confirms the loop reproduction and finds a desired image, the loop reproduction is stopped by turning ON the temporary stop button 24d, and only one desired image can be saved by the save button 24. When the operator finds a plurality of desired images, by turning ON the temporary stop button 24d and turning ON the save button 24 every time the desired images are found, a plurality of the desired images can be stored in the second storage section 14.

Figure 7:
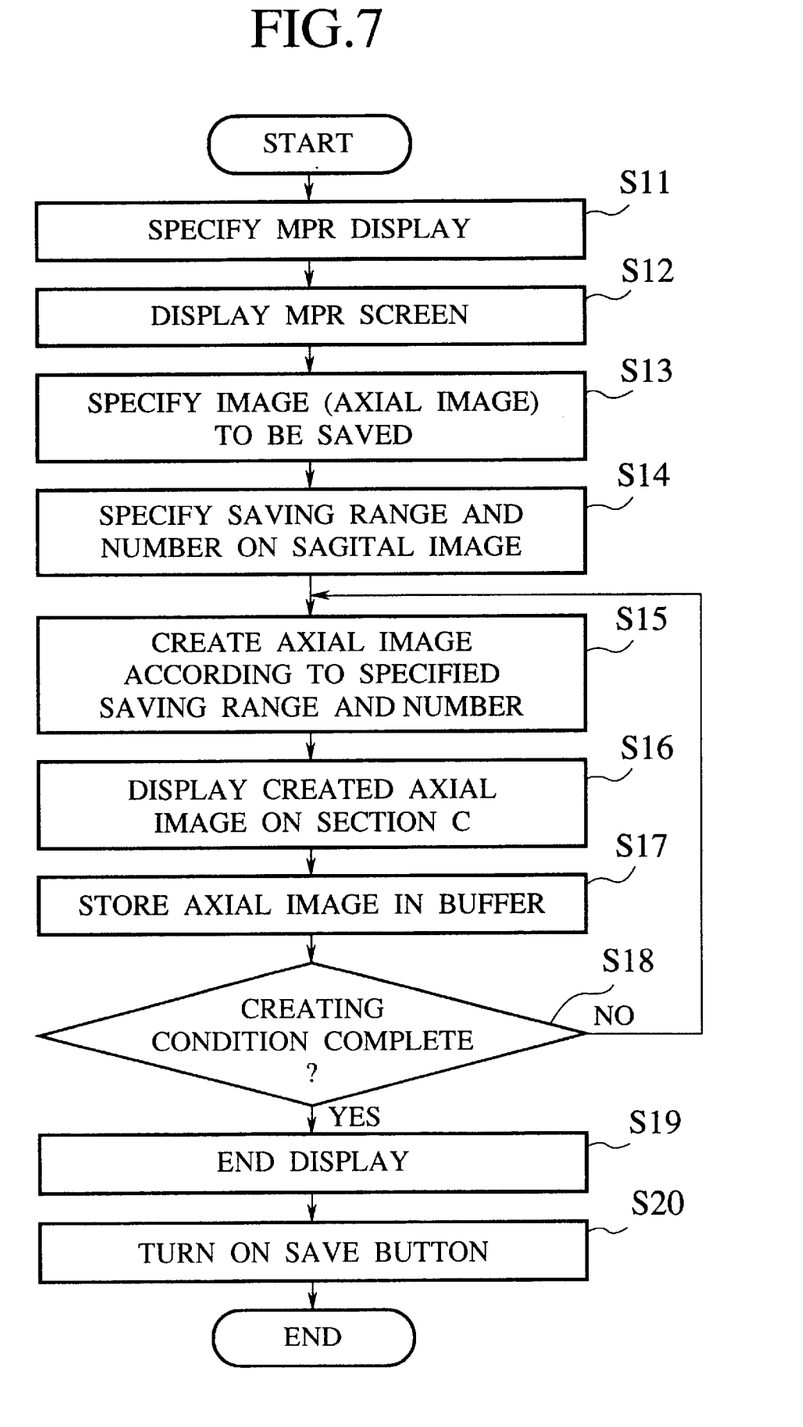
FIG. 7 is a flow chart showing a processing sequence in the case where a saving range and number are specified.

In the above explanation based on FIG. 4, "saving range" and "pitch" of the sagital image are specified as the creating condition, and corresponding number of the axial images are obtained. However, the "saving range" and "number" of the sagital image may be specified, and a plurality of axial images having the corresponding pitch may be obtained. FIG. 7 is a flow chart showing this processing sequence.

At S14, it is specified and inputted on a range specifying section 23 (FIG. 6) that a desired range of an image (axial image) to be saved is between the positions $R_{11}$ and $R_{12}$ of the sagital image on the section B, and a number of the axial images is specified and inputted (S14). At S5, the cross sectional position calculating section 11c (FIG. 3) creates the axial images according to the desired range and number (creating conditions) specified. The other processing steps are the same as those in FIG. 4.

Here, a method of specifying one end, number and pitch can be also considered.

Figure 8:
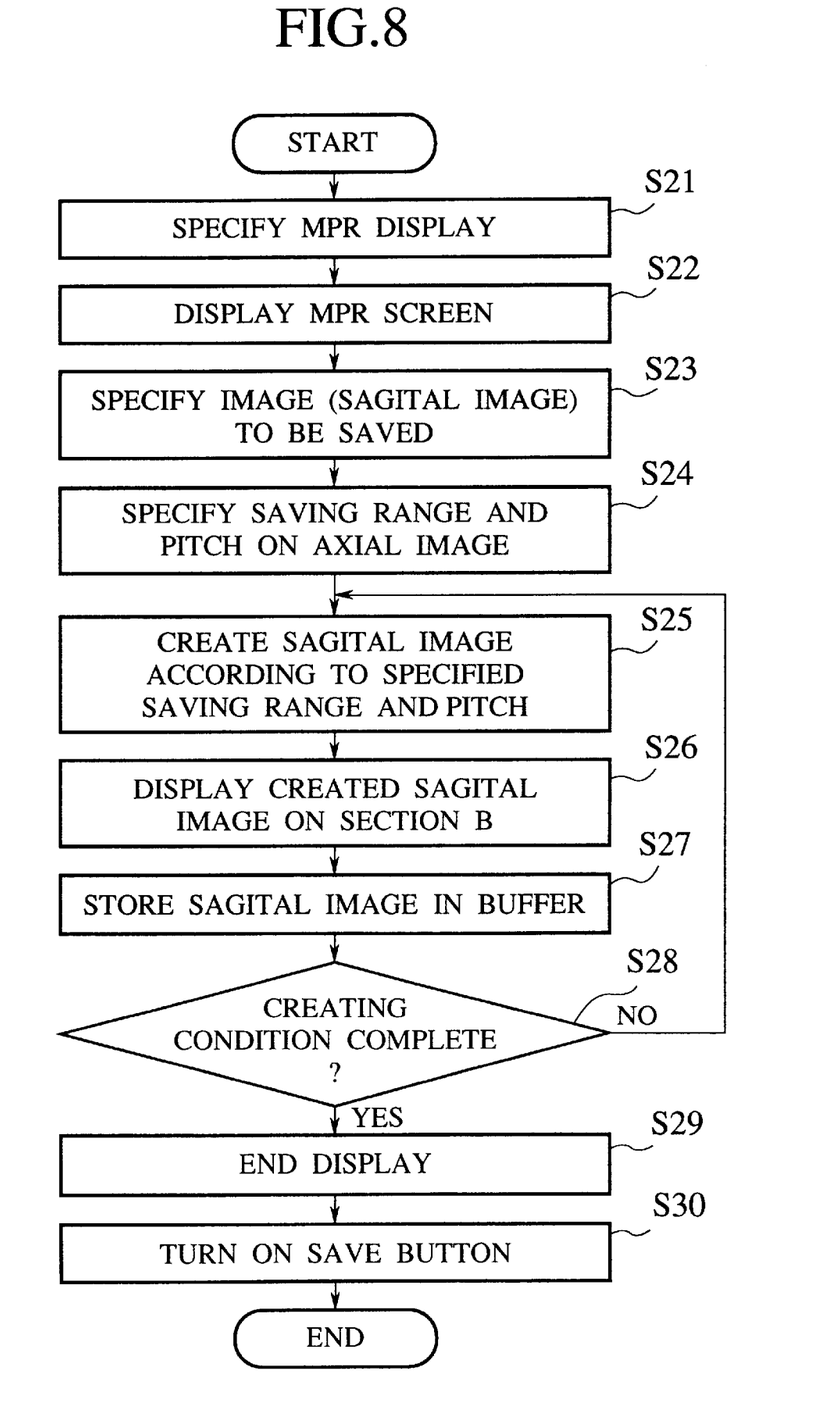
FIG. 8 is a flow chart showing a processing sequence in the case where the sagital image is specified so that the axial image is obtained.

The following describes the case where the axial image is specified so that the sagital image is obtained. FIG. 8 is a flow chart showing a processing sequence in the case where the axial image is specified so that the sagital image is obtained, and FIG. 9 is a drawing showing the display in the case where the axial image is specified so that the sagital image is obtained.

Figure 9:
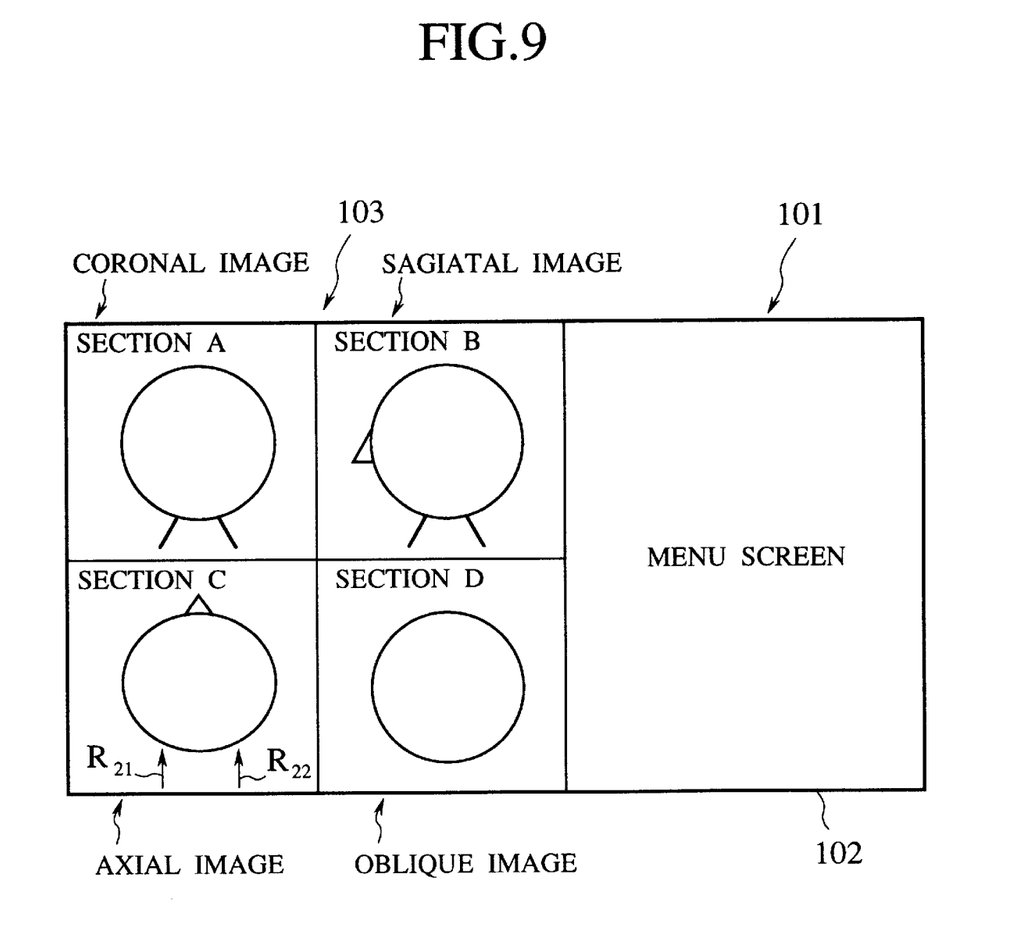
FIG. 9 is a drawing showing a display in the case where the sagital image is specified so that the axial image is obtained.

First, when an operator such as a doctor specifies MPR display on the MPR display specifying button (not shown) provided on the menu screen (FIG. 6) (S21), an MPR image shown in FIG. 9 is displayed (S22). The sagital image (section B) as an image, which is desired to be saved, is specified by turning ON a sagital button 21b (FIG. 6) through a cursor (not shown) (S23).

It is specified and inputted on the range specifying section 23 (FIG. 6) that the desired range of the image to be saved (sagital image) is between the positions $R_{21}$ and $R_{22}$ of the axial image on the section C, and the pitch of the cross sections of the sagital image is specified and inputted on the pitch specifying section 22 (S24). Then, the cross sectional position calculating section 11c (FIG. 3) creates the sagital images according to the desired range and pitch (creating conditions) specified(S25). Here, the pitch and range of the cross sections to be saved can be set arbitrarily.

Thereafter, the created first sagital image is displayed on the section B (S26), the sagital image is stored in the buffer 15 (S27), and these steps are repeated until the desired range and pitch are completed (S28).

After the steps are completed in the case of the specified creating condition (S28; YES), the completion of creating the sagital images according to the specified creating condition is displayed (S29), and when the save button 24 is turned ON, the sagital images according to the specified creating condition are simultaneously stored in the second storage section 14 (S30).

(2) Second Embodiment

The present embodiment refers to the case where a cross sectional image is specified according to a rotational angle.

Figure 10:
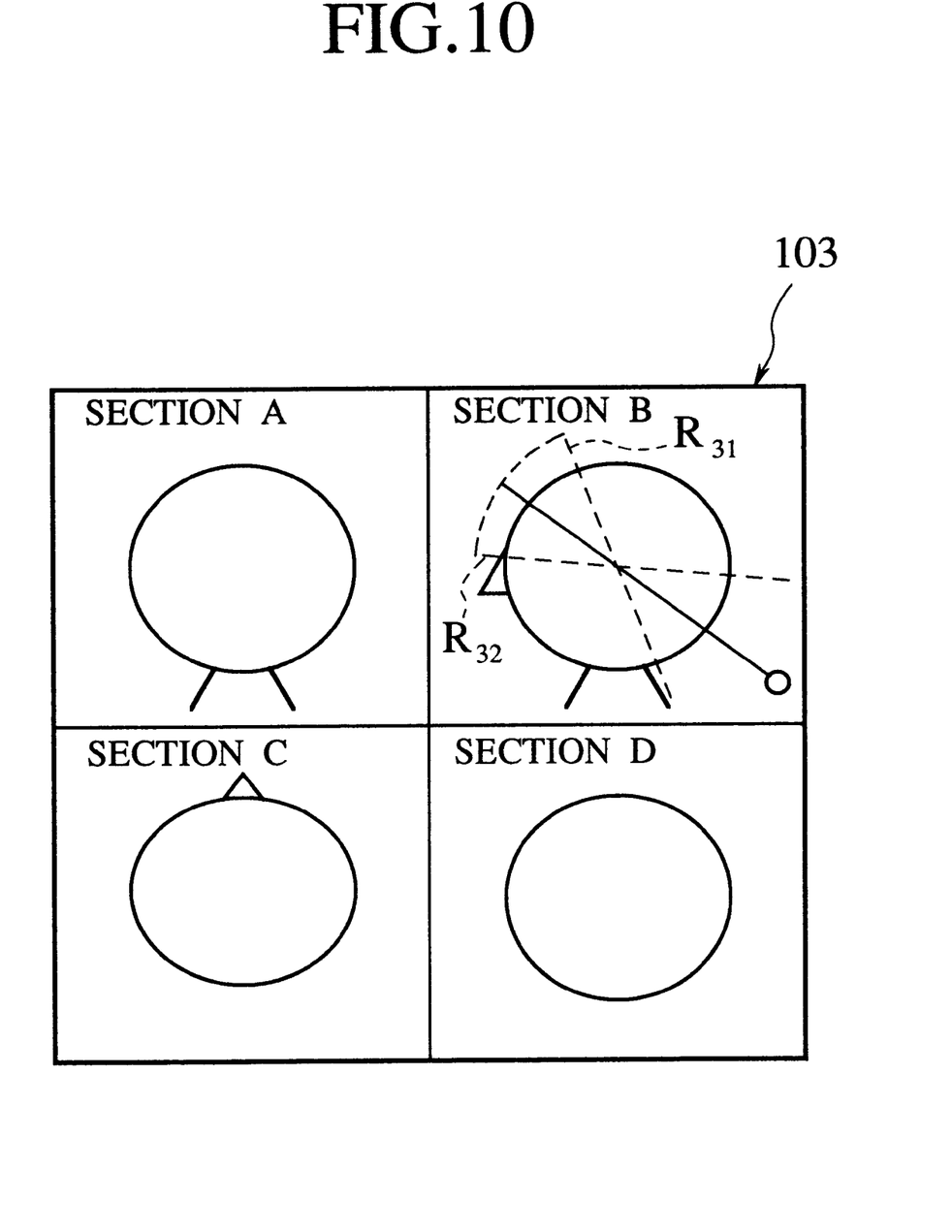
FIG. 10 is a drawing explaining a second embodiment of the MPR image creating apparatus of the present invention.

As shown in FIG. 10, for example, the sagital image is specified so that an axial image between angles $R_{31}$ and $R_{32}$ is saved.

Also in this case, similarly to the first embodiment, when the range (angles between $R_{31}$ through $R_{32}$) and pitch are specified, a desired cross sectional image (an oblique image in this case) can be automatically stored in the second storage section 14 according to the similar procedure to that shown in FIG. 4.

As described above, according to the present invention, the MPR image is displayed on the display, and when a desired MPR image (for example, axial image) is specified and a desired range is specified on a sagital image, for example, a desired number of axial images can be obtained. For this reason, a lot of desired MPR images can be obtained or saved without repetition of troublesome operations.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. AN MPR image creating apparatus, comprising:
    MPR image creating means for creating at least not less than two coaxial tomograms in different slice directions as MPR images;
    MPR image display means for displaying the MPR images created by said MPR image creating means;
    creating condition set control means for setting a creating condition of one MPR image displayed on said MPR image display means; and
    coaxial tomogram creating means for creating coaxial tomograms corresponding to the MPR image whose creating condition has been set based on the creating condition set by said creating condition set control means.

2. AN MPR image creating apparatus according to claim 1, wherein said creating condition set control means sets a range and pitch of coaxial tomograms to be obtained as the creating condition.

3. AN MPR image creating apparatus according to claim 1, wherein said creating condition set control means set a range and number of coaxial tomograms to be obtained as the creating condition.

4. AN MPR image creating apparatus according to claim 1, further comprising a buffer for temporarily storing the coaxial tomograms created by said coaxial tomogram creating means.

5. AN MPR image creating apparatus according to claim 4, further comprising coaxial tomogram display means for displaying the coaxial tomograms created by said coaxial tomogram creating means.

6. AN MPR image creating apparatus according to claim 5, wherein said coaxial tomogram display means successively displays a plurality of the coaxial tomograms stored in said buffer.

7. AN MPR image creating apparatus according to claim 6, wherein said coaxial tomogram display means comprises display speed set means for setting a display speed when said plurality of coaxial tomograms are successively displayed.

8. AN MPR image creating apparatus according to claim 6, further comprising coaxial tomogram specifying means for specifying an arbitrary coaxial tomogram of said plurality of coaxial tomograms displayed by said coaxial tomogram display means.

9. AN MPR image creating apparatus according to claim 8, further comprising storage means for storing the coaxial tomogram specified by said coaxial tomogram specifying means.

10. AN MPR image creating apparatus according to claim 1, further comprising coaxial tomogram display means for displaying the coaxial tomograms created by said coaxial tomogram creating means.

11. A coaxial tomogram creating method in an MPR image creating apparatus, comprising the steps of:

creating at least not less than two coaxial tomograms in different slice directions as MPR images;

displaying the created MPR images;

setting a creating condition of one displayed MPR image; and, creating coaxial tomograms corresponding to the MPR image whose creating condition has been set based on the creating condition.

* * * * *